United States Patent
Ito et al.

(10) Patent No.: US 11,793,391 B2
(45) Date of Patent: Oct. 24, 2023

(54) IMAGE PROCESSING DEVICE, IMAGE PROCESSING METHOD, ENDOSCOPE SYSTEM, AND ENDOSCOPE OBSERVATION METHOD

(71) Applicant: OLYMPUS CORPORATION, Tokyo (JP)

(72) Inventors: Ryosuke Ito, Tokyo (JP); Yuki Shono, Tokyo (JP); Takayuki Tsukagoshi, Tokyo (JP); Yohei Tanikawa, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 513 days.

(21) Appl. No.: 17/178,815

(22) Filed: Feb. 18, 2021

(65) Prior Publication Data

US 2021/0174510 A1    Jun. 10, 2021

Related U.S. Application Data

(63) Continuation of application No. PCT/JP2018/039131, filed on Oct. 22, 2018.

(51) Int. Cl.
*A61B 1/00* (2006.01)
*G06T 7/90* (2017.01)
(Continued)

(52) U.S. Cl.
CPC .......... *A61B 1/00057* (2013.01); *A61B 1/044* (2022.02); *A61B 1/0638* (2013.01);
(Continued)

(58) Field of Classification Search
None
See application file for complete search history.

(56) References Cited

U.S. PATENT DOCUMENTS

| 2009/0290017 A1* | 11/2009 | Shibasaki | H04N 23/56 348/71 |
| 2015/0379698 A1* | 12/2015 | Kuramoto | H04N 1/6027 382/128 |
| 2016/0220108 A1 | 8/2016 | Ono | |

FOREIGN PATENT DOCUMENTS

| EP | 3051490 A1 | 8/2016 |
| JP | S64-005525 A | 1/1989 |

(Continued)

OTHER PUBLICATIONS

International Search Report dated Jan. 15, 2019 issued in PCT/JP2018/039131.

*Primary Examiner* — Dov Popovici
(74) *Attorney, Agent, or Firm* — Scully, Scott, Murphy & Presser, P.C.

(57) ABSTRACT

An image processing device includes: one or more processors including hardware. The one or more processors are configured to: calculate, on a basis of a reference image acquired by capturing an image of a reference subject which has an optical characteristic that is equivalent to at least a part of a living body, image transformation parameters through congruence transformation that transforms a coordinate corresponding to a color of target region included in the reference image defined in a color space into a coordinate corresponding to an achromatic color in the color space; and perform, in the color space on a basis of the calculated image transformation parameters, the congruence transformation of colors of a color image acquired by capturing an image of the living body, the color image being constituted by at least two monochromatic image corresponding to different illumination having different center wavelengths.

16 Claims, 14 Drawing Sheets

(51) Int. Cl.
*A61B 1/06* (2006.01)
*A61B 5/00* (2006.01)
*G06T 7/00* (2017.01)
*H04N 1/60* (2006.01)
*A61B 1/04* (2006.01)

(52) U.S. Cl.
CPC ............ *A61B 5/489* (2013.01); *G06T 7/0014* (2013.01); *G06T 7/90* (2017.01); *H04N 1/6016* (2013.01); *G06T 2207/10024* (2013.01); *G06T 2207/10068* (2013.01); *G06T 2207/30101* (2013.01)

(56) References Cited

FOREIGN PATENT DOCUMENTS

| | | |
|---|---|---|
| JP | H04-329753 A | 11/1992 |
| JP | 3121368 B2 | 12/2000 |
| JP | 2006-271871 A | 10/2006 |
| JP | 2009-279150 A | 12/2009 |
| JP | 2014-124484 A | 7/2014 |
| JP | 2015-198890 A | 11/2015 |
| JP | 2016-010506 A | 1/2016 |
| JP | 2016-140428 A | 8/2016 |
| JP | 2016-206301 A | 12/2016 |
| JP | 6121368 B2 | 4/2017 |

\* cited by examiner

IMAGE PROCESSING DEVICE, IMAGE PROCESSING METHOD, ENDOSCOPE SYSTEM, AND ENDOSCOPE OBSERVATION METHOD

CROSS-REFERENCE TO RELATED APPLICATIONS

This is a continuation of International Application PCT/JP2018/039131, with an international filing date of Oct. 22, 2018, which is hereby incorporated by reference herein in its entirety.

TECHNICAL FIELD

The present invention relates to an image processing device, an image processing method, an endoscope system, and an endoscope observation method.

BACKGROUND ART

There are well-known medical image processing devices for generating images in which the color difference between an abnormal site, such as an atrophic site of the gastric mucosa, and a normal site is emphasized (for example, refer to PTL 1).

In the medical image processing device in PTL 1, an original image is transferred in any color space in a way that a first region, a second region, and a third region of an observation target are defined in the color space, then the second region is moved to a reference region with low chroma in the color space, and at least one of the first region and the third region is moved to other region in the color space.

CITATION LIST

Patent Literature

PTL 1
Publication of Japanese Patent No. 3121368

SUMMARY OF INVENTION

One aspect of the present invention is directed to an image processing device including: one or more processors comprising hardware, the one or more processors being configured to: calculate, on a basis of a reference image acquired by capturing an image of a reference subject which has an optical characteristic that is equivalent to at least a part of a living body, image transformation parameters through congruence transformation that transforms a coordinate corresponding to a color of target region included in the reference image defined in a color space into a coordinate corresponding to an achromatic color in the color space; and perform, in the color space on a basis of the calculated image transformation parameters, the congruence transformation of colors of a color image acquired by capturing an image of the living body, the color image being constituted by at least two monochromatic image corresponding to different illumination having different center wavelengths.

Another aspect of the present invention is directed to an image processing method including: calculating, on a basis of a reference image acquired by capturing an image of a reference subject which has an optical characteristic that is equivalent to at least a part of a living body, image transformation parameters through congruence transformation that transforms a coordinate corresponding to a color of target region included in the reference image defined in a color space into a coordinate corresponding to an achromatic color in the color space; and performing, in the color space on a basis of the image transformation parameters obtained by calculation, the congruence transformation of colors of a color image acquired by capturing an image of the living body, the color image being constituted by at least two monochromatic image corresponding to different illumination having different center wavelengths.

Another aspect of the present invention is directed to an endoscope system including: an endoscope that acquires the color image by capturing an image of the living body; and one of the above-described image processing devices, wherein the calculating of the image transformation parameters calculates the parameter on a basis of the reference image acquired by capturing an image of the reference subject by means of the endoscope, and the performing of the congruence transformation transforms the colors of the color image acquired by the endoscope.

Another aspect of the present invention is directed to an endoscope observation method including: acquiring a reference image by capturing, by means of an endoscope, an image of a reference subject which has an optical characteristic that is equivalent to at least a part of a living body; calculating, on a basis of the acquired reference image, image transformation parameters through congruence transformation that transforms a coordinate corresponding to a color of a target region included in the reference image defined in the color space into a cooridinate corresponding to an achromatic color in the color space; acquiring a color image constituted by at least two monochromatic image corresponding to different illumination having different center wavelengths by capturing an image of the living body by means of the endoscope; performing the congruence transformation of all colors of the acquired color image in the color space on a basis of the image transformation parameters acquired by calculation; and displaying an image that has been subjected to the congruence transformation.

DESCRIPTION OF EMBODIMENTS

An image processing device 3, an image processing method, an endoscope system 1, and an endoscope observation method according to one embodiment of the present invention will now be described with reference to the drawings.

Figure 1:
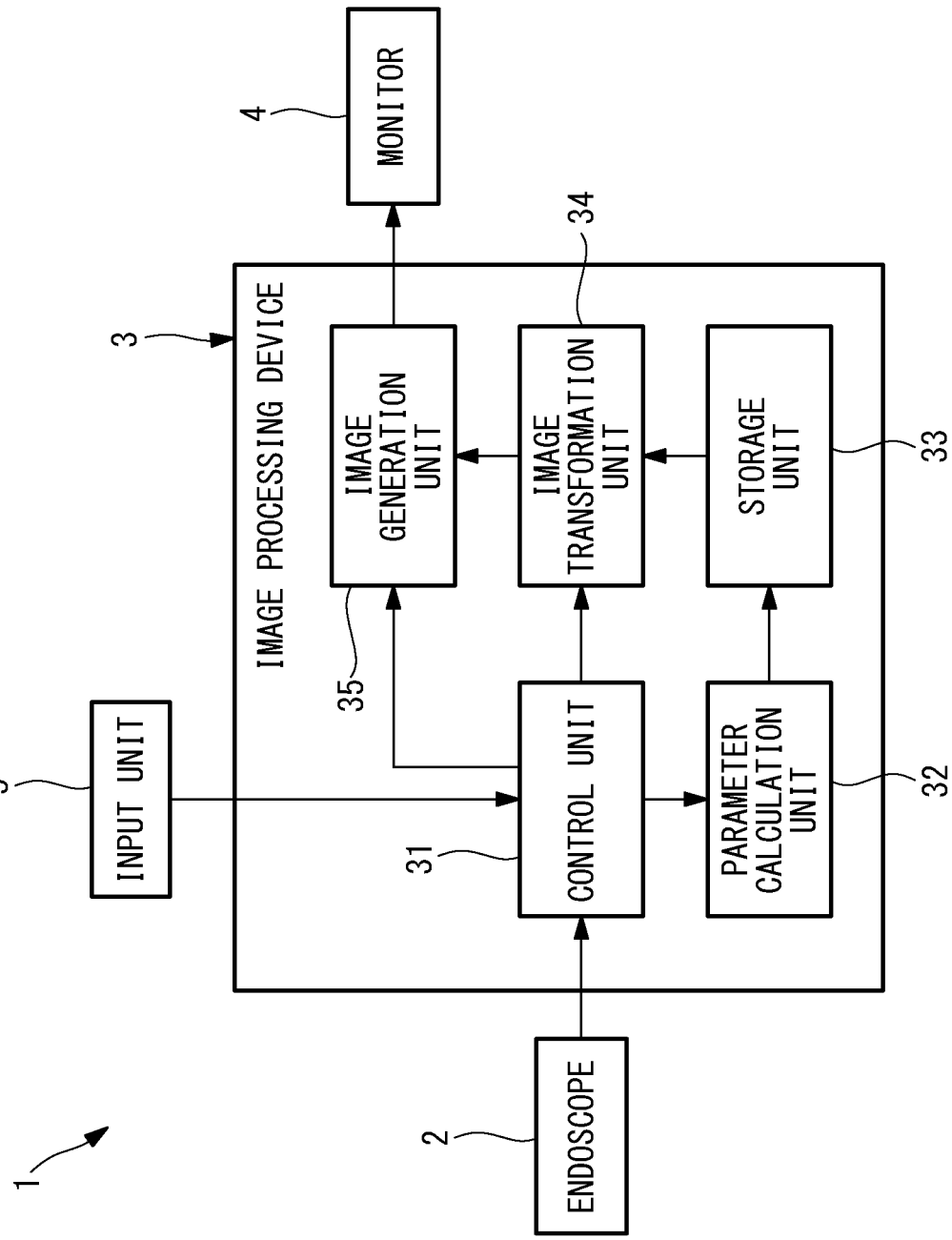
FIG. 1 is a block diagram showing an endoscope system and an image processing device according to one embodiment of the present invention.

As shown in FIG. 1, the image processing device 3 according to this embodiment is included in the endoscope system 1.

As shown in FIG. 1, the endoscope system 1 according to this embodiment includes: an endoscope (image-capturing unit) 2 that acquires a color image (refer to FIG. 2) C by capturing an image of a subject (living body); the image processing device 3 for processing the color image C acquired by the endoscope 2; a monitor 4 for displaying the image; and an input unit 5 for allowing a technician to perform input. The input unit 5 is an input device, such as a keyboard, a mouse, or a touch panel.

As shown in FIG. 1, the image processing device 3 includes a control unit 31; a parameter calculation unit 32; a storage unit 33; an image transformation unit (transformation unit) 34; and an image generation unit 35. The control unit 31, the parameter calculation unit 32, the image transformation unit 34, and the image generation unit 35 are configured from processors, and the storage unit 33 is configured from a memory.

The image generation unit 35 generates images to be displayed on the monitor 4.

On the basis of a reference image acquired by the endoscope 2, the parameter calculation unit 32 calculates a parameter for congruence-transforming, into an achromatic color in a color space, a color corresponding to a target region in the reference image defined in the color space. Here, an achromatic color is white, black, and a color obtained by mixing white and black, i.e., a color containing gray with various color densities. In addition, congruence transformation in this embodiment indicates transformation that does not cause the distance between two arbitrary points to be changed in Euclidean space.

The storage unit 33 stores the parameter calculated by the parameter calculation unit 32.

By using the parameter stored in the storage unit 33, the image transformation unit 34 transforms a color image C acquired by capturing an image of the living body by means of the endoscope 2.

Figure 2:
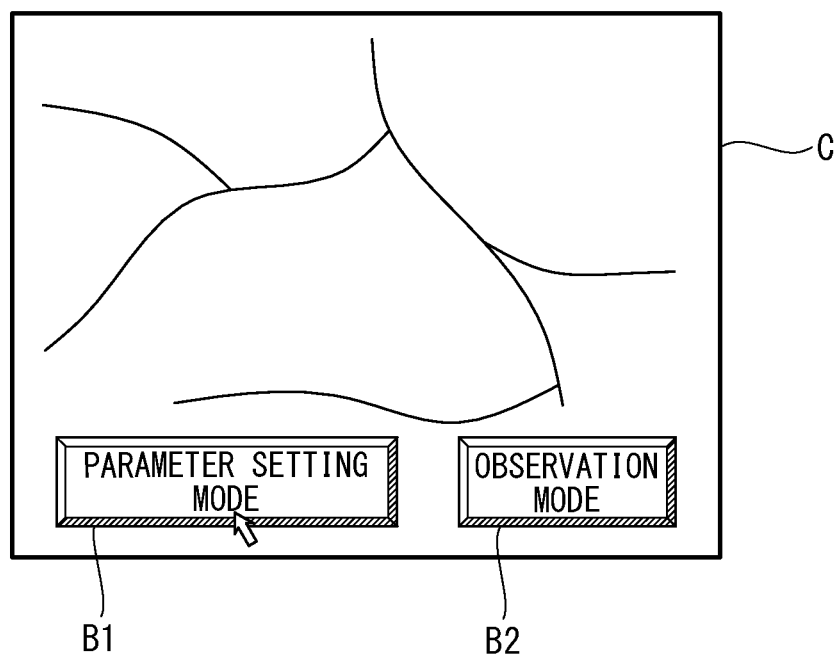
FIG. 2 is a diagram showing an example of an image displayed using the image processing device in FIG. 1.

The control unit 31 controls the image generation unit 35, the parameter calculation unit 32, and the image transformation unit 34 on the basis of input from the input unit 5. For example, the control unit 31 displays, on the monitor 4, buttons B1 and B2 for selecting a mode by means of a GUI, as shown in FIG. 2, and when the technician selects one of the buttons B1 and B2 by operating the input unit 5, the control unit 31 performs control according to the content of the selected button B1 or B2.

Figure 3:
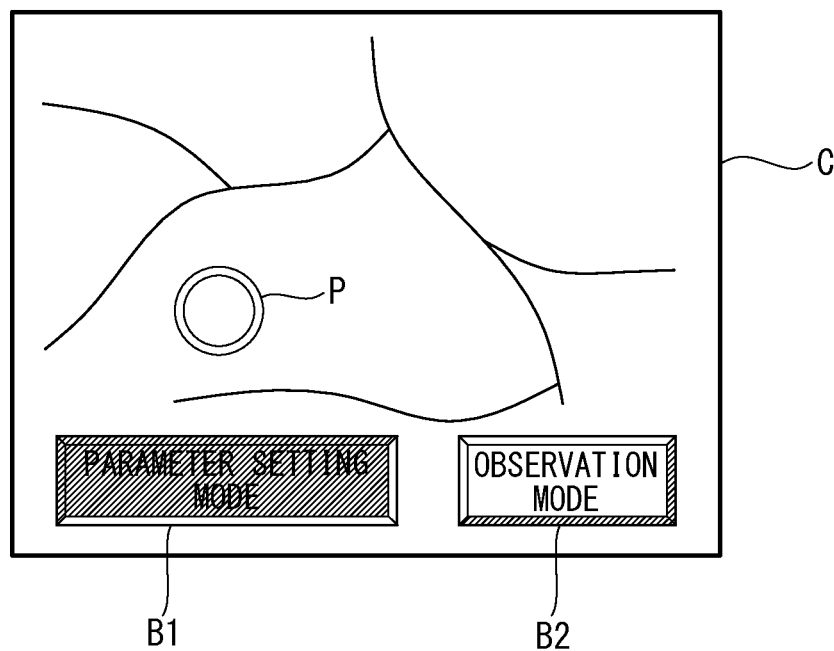
FIG. 3 is a diagram showing an example of a display image in the case where a parameter setting mode is selected in the image in FIG. 2.

More specifically, the control unit 31 inputs the color image C acquired by the endoscope 2 to the image generation unit 35, thereby not only preparing the color image C as a display image to be displayed on the monitor 4 but also preparing the mode-selecting buttons B1 and B2 on the display image. Also, when the parameter-setting-mode button B1 displayed on the monitor 4 is selected, the control unit 31 displays a pointer P for specifying a target region on the monitor 4, as shown in FIG. 3. The pointer P can be moved to any position on the color image C displayed on the monitor 4 through the operation of the input unit 5, thereby allowing the technician to specify a desired region as a target region.

In addition, when a target region is specified by means of the pointer P, the control unit 31 sends, to the parameter calculation unit 32, color information of that target region in the color space.

The parameter calculation unit 32 calculates a parameter for congruence-transforming, into an achromatic color in the color space, the color indicated by the color information sent from the control unit 31. The calculated parameter is stored in the storage unit 33.

Figure 4:
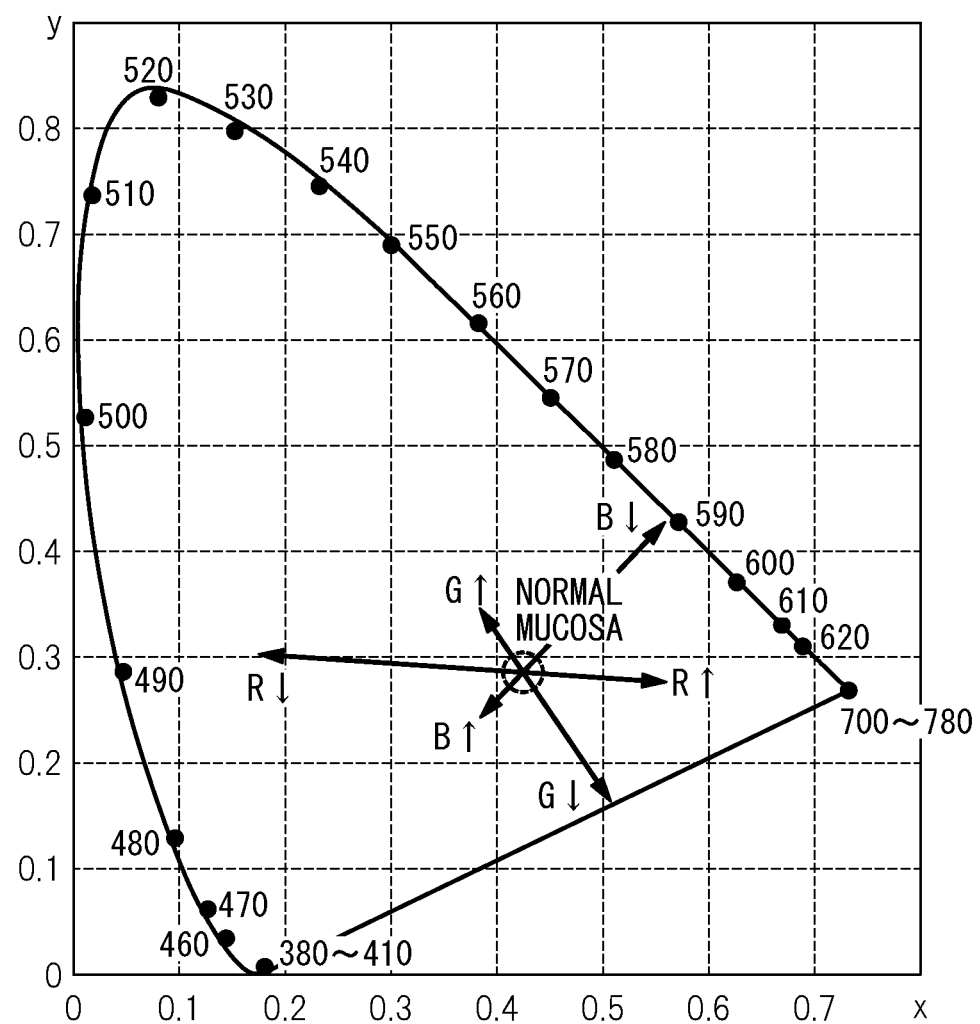
FIG. 4 is one example of a color space showing the position of a color of a normal mucosa, said position being set through calibration by means of a conventional white color board.
Figure 5:
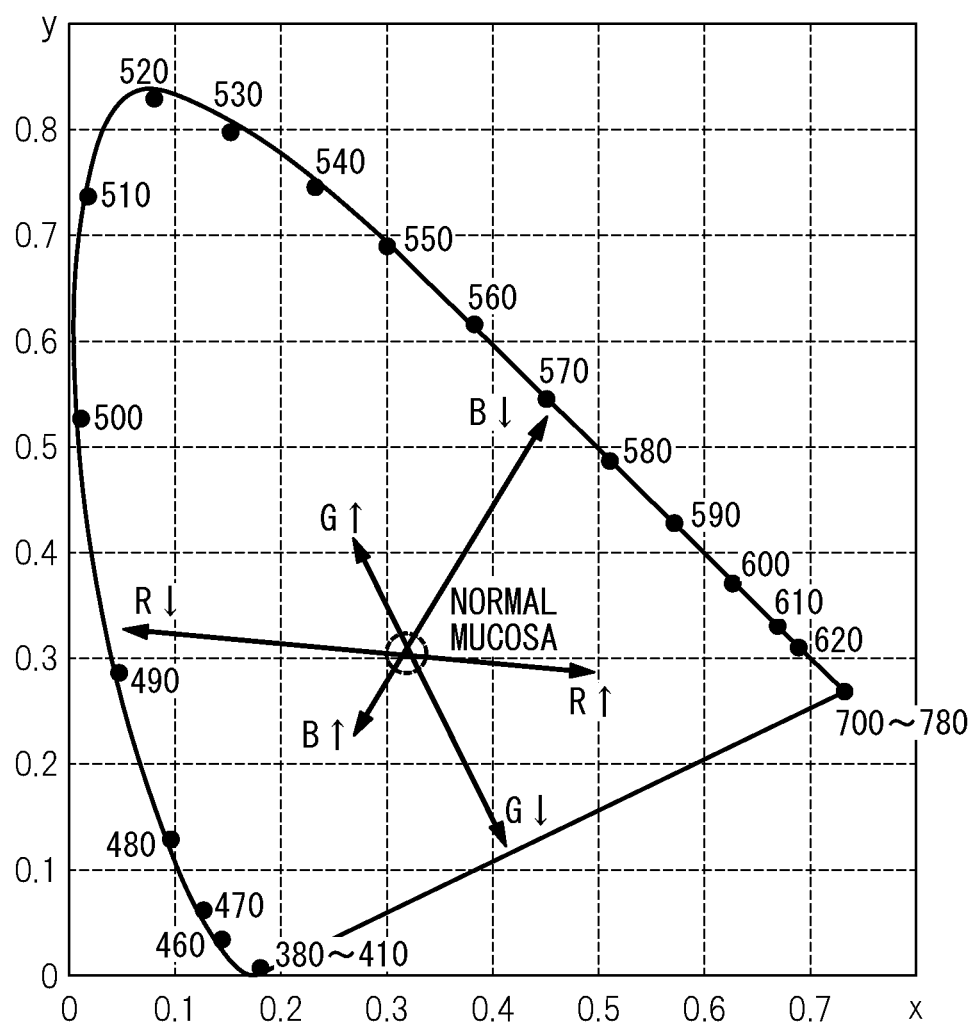
FIG. 5 is a color space showing the position of a color of a normal mucosa, said position being set by the image processing device in FIG. 1.

More specifically, in the case of calibration by means of a conventional white color board, the color of a normal mucosa is made to correspond to a light red color, as shown in FIG. 4, in order to maintain color reproducibility of mucosae in organs. The parameter calculation unit 32 calculates a parameter for congruence-transforming the color of this normal mucosa into a white color (achromatic color) in the color space, as shown in FIG. 5. Here, any color space having arbitrary color space coordinates, such as RGB, XYZ, CMY, or Lab, may be employed as the color space. Examples of the parameter include the difference coefficient at each color space coordinate between the color of the specified target region in the color space and the achromatic color.

Figure 6:
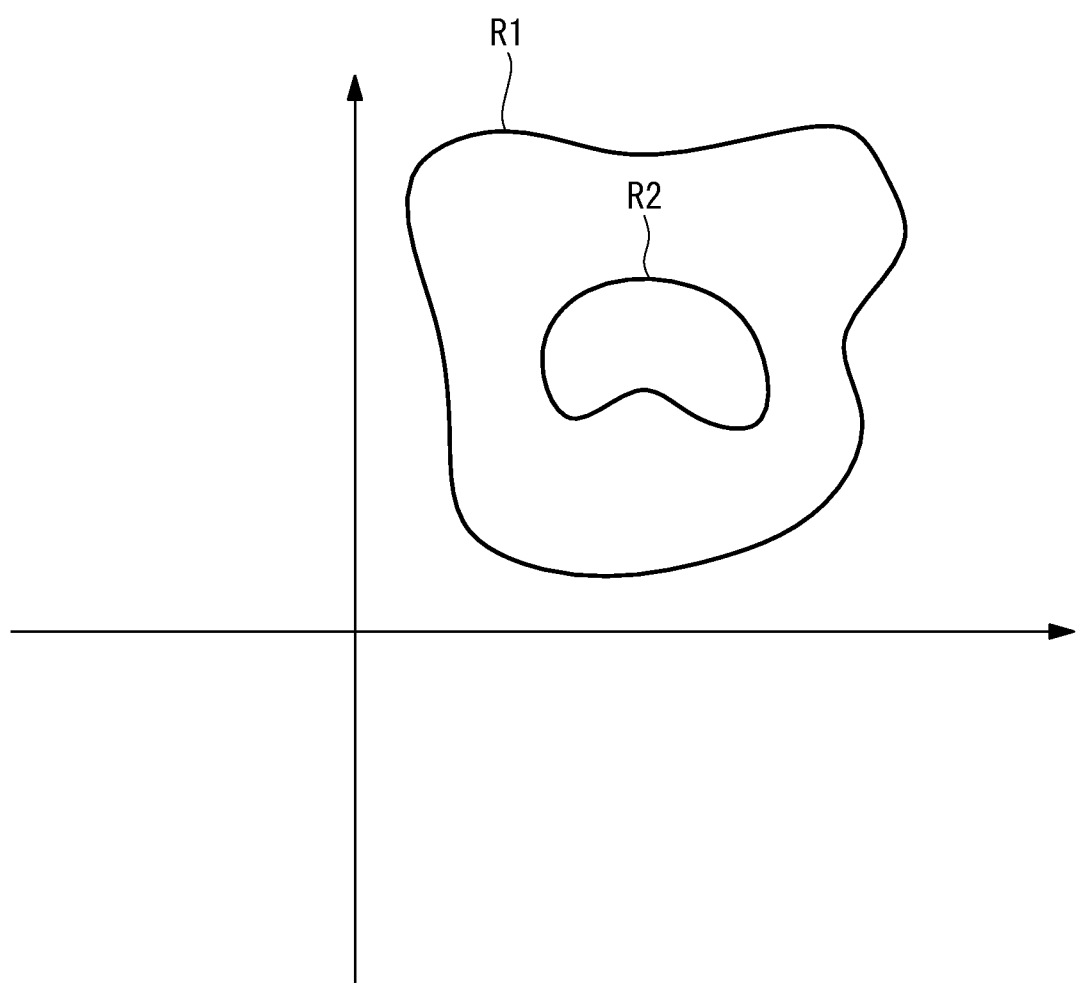
FIG. 6 is a diagram showing one example of the position of a color of biological tissue in a color space, said position being set through calibration by means of a conventional white color board.
Figure 7:
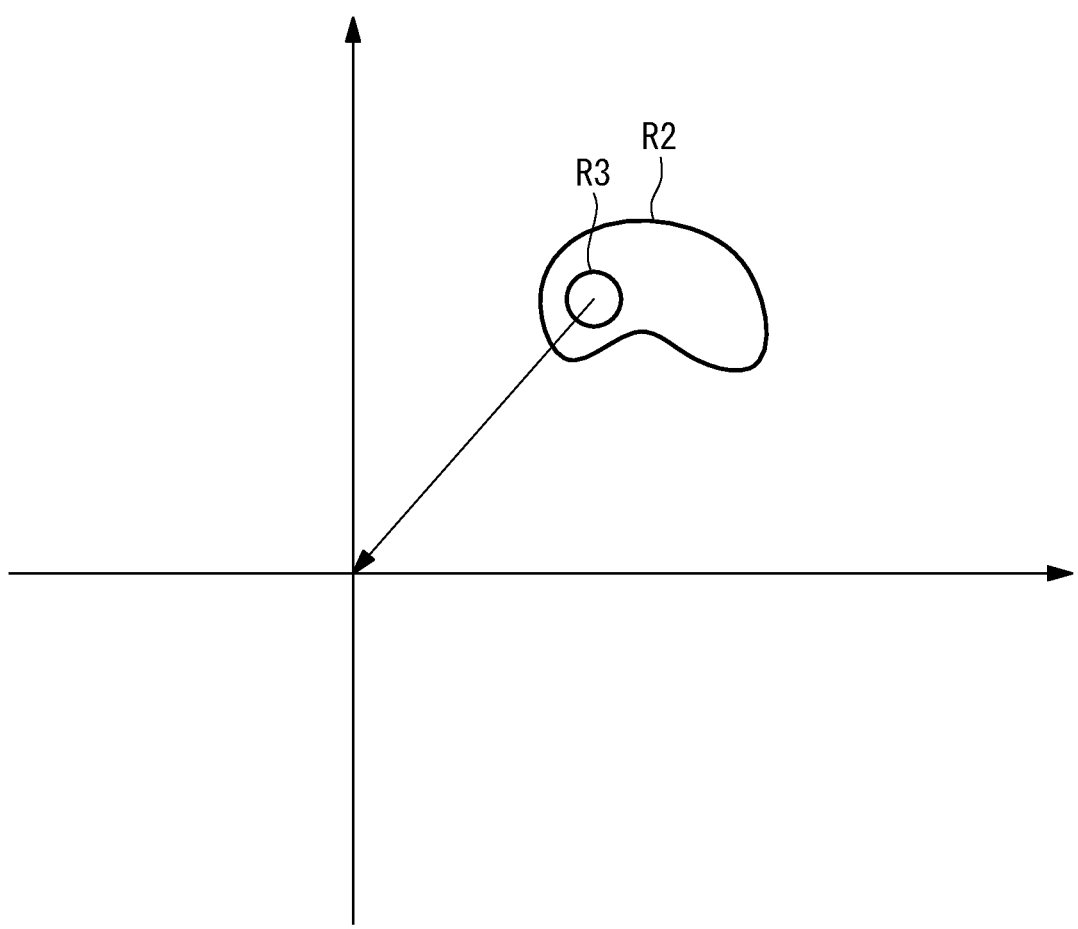
FIG. 7 is a diagram showing one example of the position of a color, in a color space, of a target region included in a reference image in FIG. 6.
Figure 8:
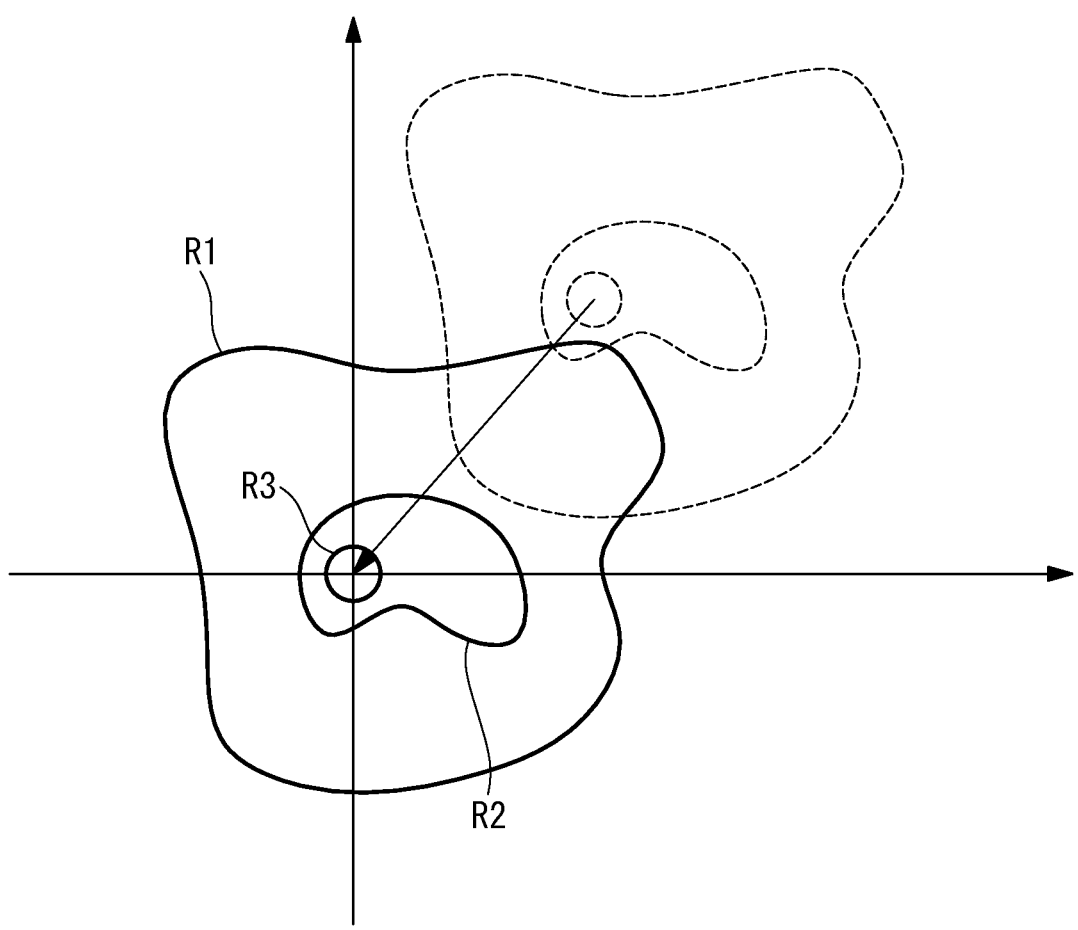
FIG. 8 is a diagram showing one example of image transformation performed by the image processing device in FIG. 1.

More specifically, as shown in, FIG. 6, a first region R1 of colors that are possible during observation with the endoscope 2 is present in the color space, and a second region R2 of colors included in the reference image is present in the first region R1. In addition, as shown in FIG. 7, a third region R3 indicating the target region is present in the second region R2. The entire first region, i.e., all colors of the color image can be parallel displaced, as shown in FIG. 8, by applying, to the entire first region R1, a parameter for congruence-transforming the color at the center of the gravity of the third region R3 into a white color located at the origin of the color space.

Thereafter, when the observation-mode button B2 displayed on the monitor 4 is selected through the operation of the input unit 5, the control unit 31 sends, to the image transformation unit 34, the color images C sequentially acquired by the endoscope 2, and the image transformation unit 34 performs transformation processing for parallel displacement of all colors of the color images C by using the parameter stored in the storage unit 33. The transformation-processed images are sent to the image generation unit 35 and are prepared as display images. As the display images, transformation-processed color images C may be employed, instead of the color images C acquired by the endoscope 2, or alternatively, the transformation-processed color images C may be displayed along with the color images C acquired by the endoscope 2.

An endoscope observation method for observing the interior of an organ of a patient by using the endoscope system 1 according to this embodiment with the above-described structure, as well as an image processing method by using the above-described image processing device 3, will be described below.

Figure 9:
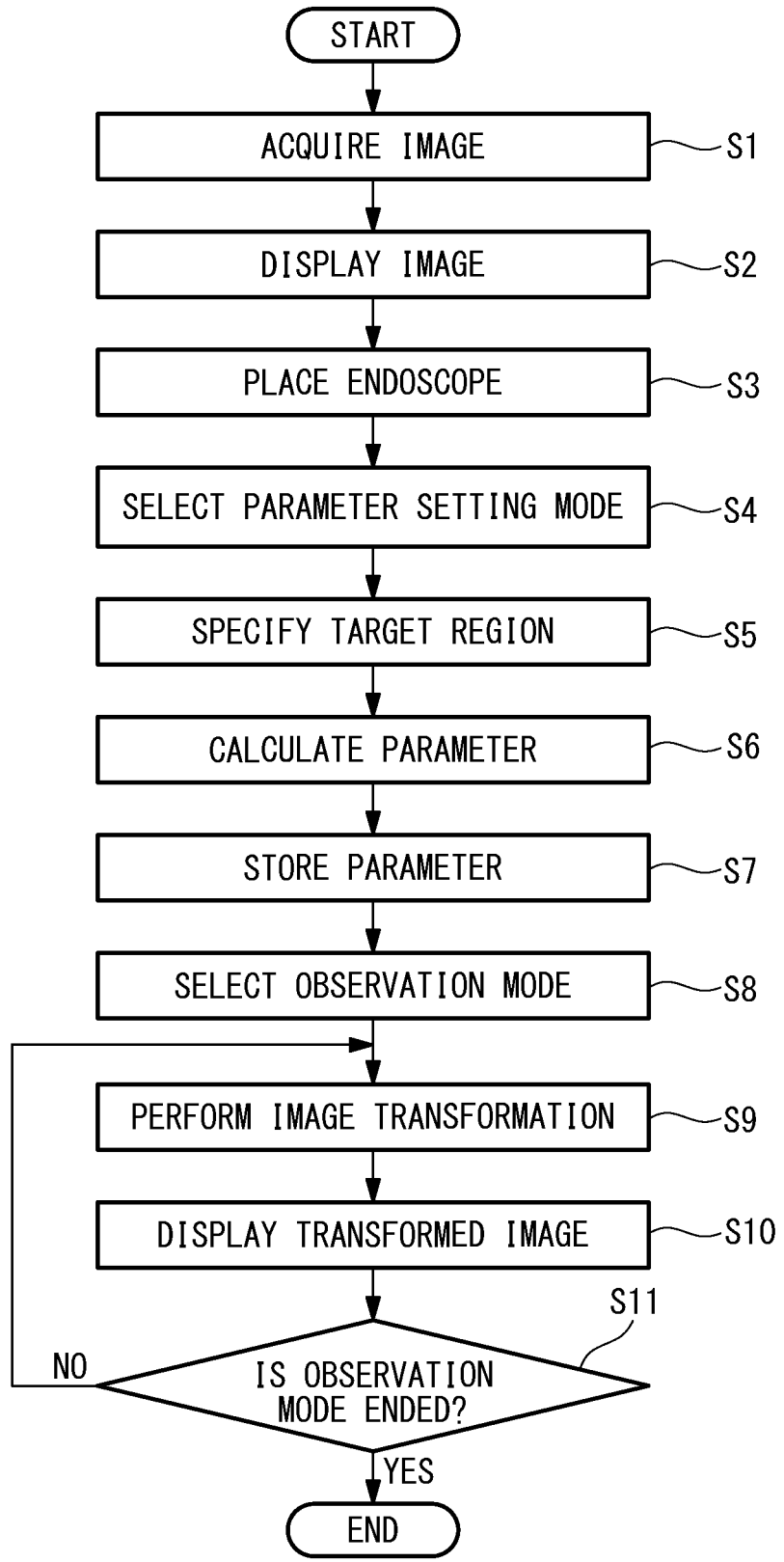
FIG. 9 is a flowchart for illustrating an endoscope observation method by means of the endoscope system in FIG. 1.

As shown in FIG. 9, in the endoscope observation method according to this embodiment, the technician inserts the endoscope 2 into an organ of a patient and acquires an image of the inner surface of the organ by means of the endoscope 2 (step S1), and the acquired image is displayed on the monitor 4 (step S2). The technician operates the endoscope 2 while observing the acquired image to place the endoscope 2 in the field of view including a normal mucosa (step S3). In this state, the technician selects the parameter setting mode by means of the input unit 5 (step S4) and specifies a normal mucosa region (target region) on the color image C by means of the pointer P displayed on the monitor 4 (step S5).

By doing so, color information at each of the color space coordinates of the normal mucosa is input to the parameter calculation unit 32. The parameter calculation unit 32 calculates a parameter by calculating the difference between the color information of the input normal mucosa and the color information of an achromatic color (step S6). The calculated parameter is stored in the storage unit 33 (step S7). If another parameter is already stored, the stored parameter is updated.

When the technician selects the observation mode in this state by operating the input unit 5 (step S8), images acquired by the endoscope 2 are sequentially input to the image transformation unit 34, the image transformation unit 34 performs transformation processing of the color images C by using the parameter stored in the storage unit 33 (step S9), and the transformation-processed images are displayed on the monitor 4 (step S10). Then, the process steps from step S9 are repeated until the technician performs input to exit the observation mode (step S11).

Because the parameter calculated in the parameter calculation unit 32 is used to transform a color of the normal mucosa in the organ into an achromatic color, transforming the entire color image C of the organ by using this parameter causes the normal mucosa portion in the color image C to be transformed into an achromatic color and causes the other portion to be transformed into a color other than the achromatic color. In other words, the color of the normal mucosa and the color of an abnormal site, though slightly different, are both based on a reddish color in the color image C of the organ and are thus difficult to discriminate from each other, but transformation by means of the above-described parameter allows the slight color difference between the normal mucosa and the abnormal site to be rendered as a difference between an achromatic color and a chromatic color, thereby making it possible to clearly identify the boundary between the normal mucosa and the abnormal site.

Furthermore, according to this embodiment, instead of performing nonlinear transformation in which only a particular color of the color image C is emphasized and imaged, the entire color image C is shifted while the distance in the color space between an abnormal site and a normal site (reference subject) is retained. Therefore, this embodiment affords an advantage in that it is possible to prevent the boundary between the abnormal site and the normal site to be rendered in an extreme color difference, thereby facilitating visual recognition of subtle changes in the hue of the living body while maintaining stability in the accuracy of the physician's diagnosis.

Although the technician specifies a target region in the reference image in this embodiment, instead of this, for example, the center of gravity or the center point of the frequency distribution of the colors constituting the reference image in the color space may be automatically set as a color of the target region. In this case, an image acquired in a state in which only a normal mucosa is likely to be present in the field of view should be preferably used as the reference image.

In addition, although the colors of the entire color image C are parallel displaced (translated) in the color space in this embodiment, instead of, or in addition to, this, the colors of the entire color image C may be rotationally moved in the color space. This also allows the normal site to be transformed into an achromatic color while retaining the distance between the abnormal site and the normal site, thereby making it possible to clarify the boundary between the abnormal site and a normal site.

In addition, although a target region is specified to calculate a parameter by using a color of the specified target region, instead of this, the parameter may be updated for each observation by tracking the position of the target region that was specified before.

In addition, although a normal mucosa has been given as an example of the target region, any region for which a color tone difference is to be emphasized may be specified. For example, a region to be specified, although it may be a normal mucosa region, can be a region including less blood vessels, whereby blood vessels are emphasized. If a blood vessel site is specified, a subtle difference in a state, such as a hyperplastic state, from a mucosa tissue site including no blood vessels is rendered as a change in color. In addition, the present embodiment may be used to emphasize a difference between tissue sites, instead of emphasizing an abnormal site, such as a lesion. For example, scar tissue (abnormal tissue) is emphasized by specifying a normal mucosa around the scarred tissue. Furthermore, when the difference between nerve membrane tissue and fat tissue (fat site) is to be emphasized, it is sufficient that a parameter for transforming the color of the fat tissue into an achromatic color is calculated.

Figure 10:
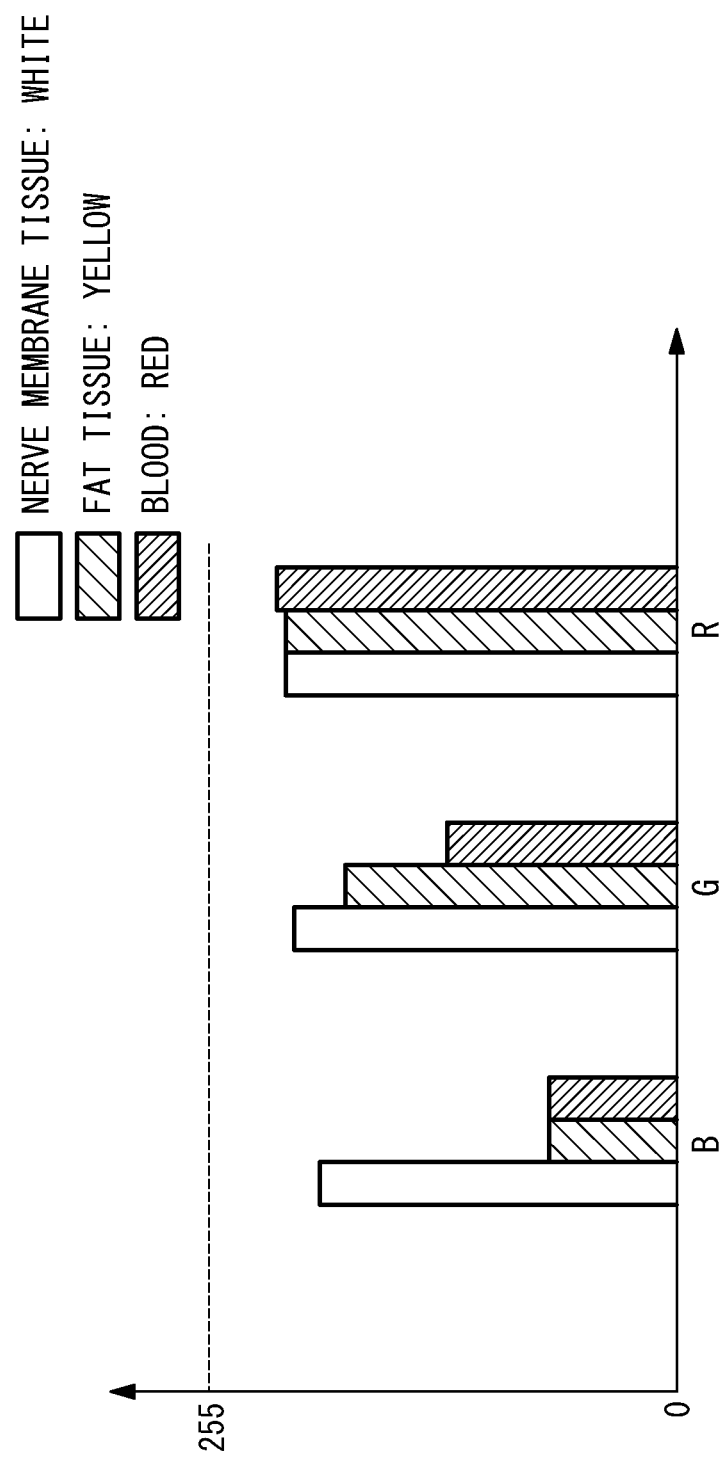
FIG. 10 is a diagram showing one example of a luminance distribution of an image acquired by an endoscope.
Figure 11:
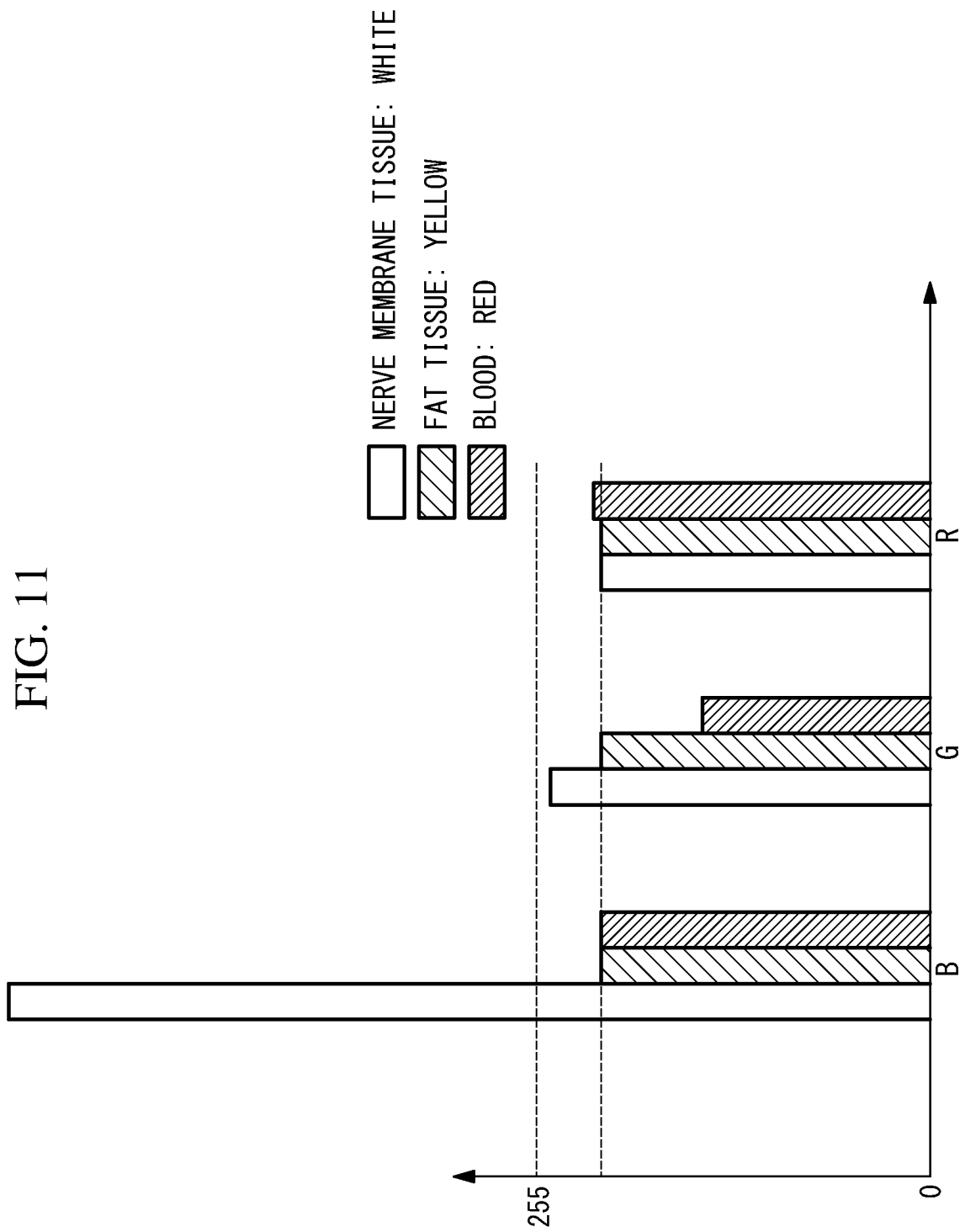
FIG. 11 is a diagram showing one example of a luminance distribution of an image resulting from the image in FIG. 10 being subjected to image transformation performed by the image processing device in FIG. 1.
Figure 12:
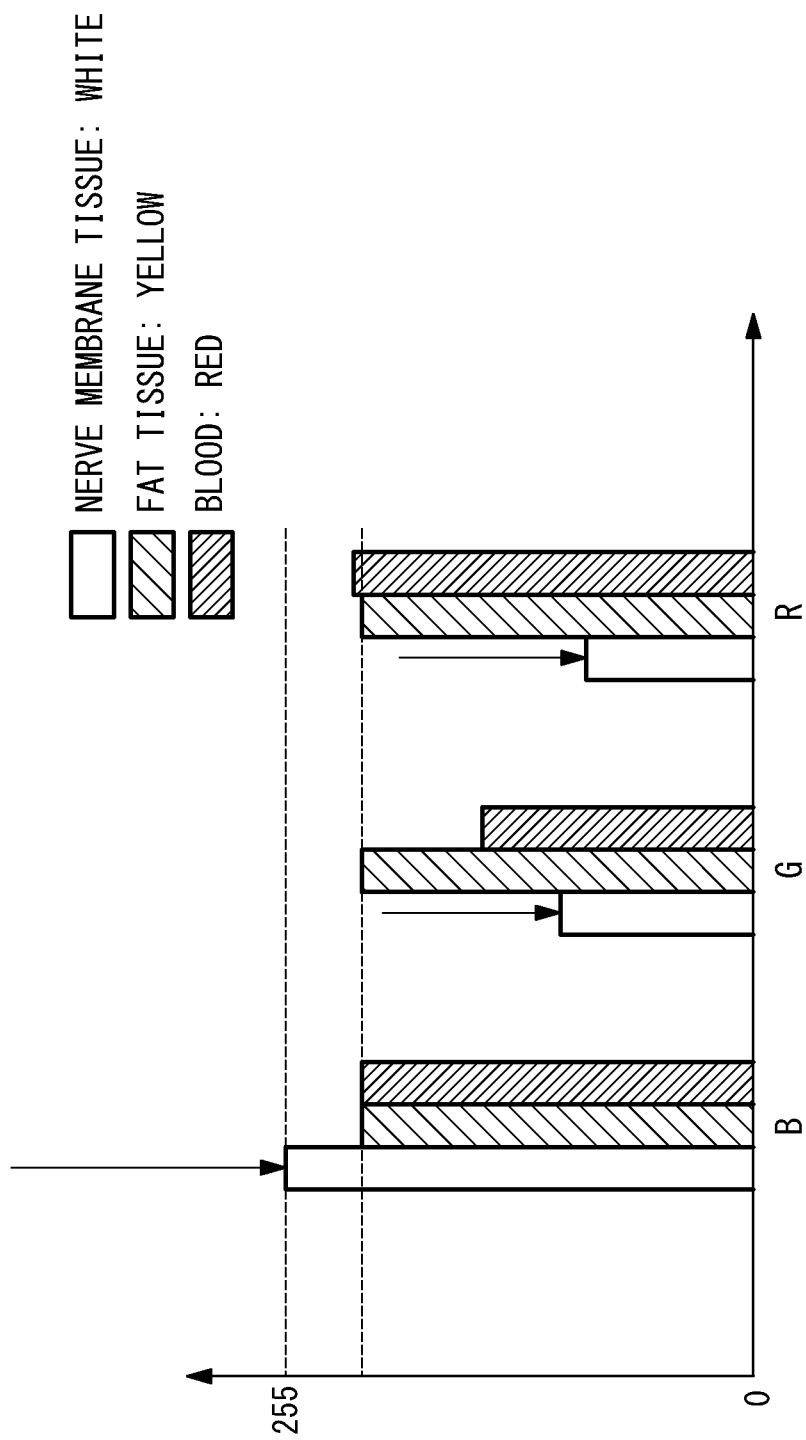
FIG. 12 is a diagram showing one example of a luminance distribution of an image resulting from the image in FIG. 11 being subjected to whiteout-prevention processing.

For example, in the case where nerve membrane tissue, fat, and blood have a white color, a yellow color, and a red color, respectively, for conventional calibration, the colors have the luminance distribution shown in FIG. 10. In this case, when the entire image is subjected to image transformation by using a parameter that sets the fat, which is originally a dark portion, to an achromatic color (white color), nerve membrane tissue, which is originally bright, suffers from whiteout, as shown in FIG. 11. In short, the blue color is saturated. If this is the case, as shown in, FIG. 12, the colors can be transformed without producing continuous whiteout by decreasing the range of color scale of the green color and the red color by the amount by which the blue color exceeds the maximum range of color scale.

In addition, although, in this embodiment, an image of the inner surface of an actual organ is acquired, and the technician is made to specify a target region presumed to be a normal mucosa, instead of this, a color of a target region may be acquired by capturing an image of a phantom F, serving as a subject (reference subject) mimicking the optical characteristics of a living body.

Examples of the phantom F include a product formed by a resin kneaded with scattering particles, serving as a scatterer, and an absorbing pigment. According to such a phantom F, the concentrations of the scattering particles and the absorbing pigment can be adjusted so that the amount of reflected light in response to radiated light and the amount of transmitted light in response to the radiated light become equivalent to those of the biological tissue of an observation subject. In addition, by adjusting the particle sizes of the scattering particles, the distribution of scattered light can be adjusted so as to be equivalent to that of biological tissue, serving as the observation subject.

In addition, a parameter used in the image transformation unit 34 can be stably calculated even if the endoscope 2 for acquiring images is replaced with another one. In addition, temporal changes in characteristics of the living body can also be captured with high accuracy by calculating a transformation parameter by using the phantom F with stable characteristics. This makes it easier for the physician to determine disease conditions and do post-therapy follow-up.

In addition, because the parameter for a component constituting the phantom F corresponds to the optical characteristics of the phantom F, a component of the living body can be simulatively estimated from an image generated on the basis of a parameter that is obtained by using the phantom F and that is used in the image transformation unit 34. This can assist the physician in diagnosis by analogically inferring a change in the pathological structure of the living body.

In addition, an object with the following aspects may be employed as the phantom F.

A surface irradiated with light emitted from the endoscope 2 is preferably flat and smooth. This can suppress diffused reflection from the surface of the phantom.

Figure 13:
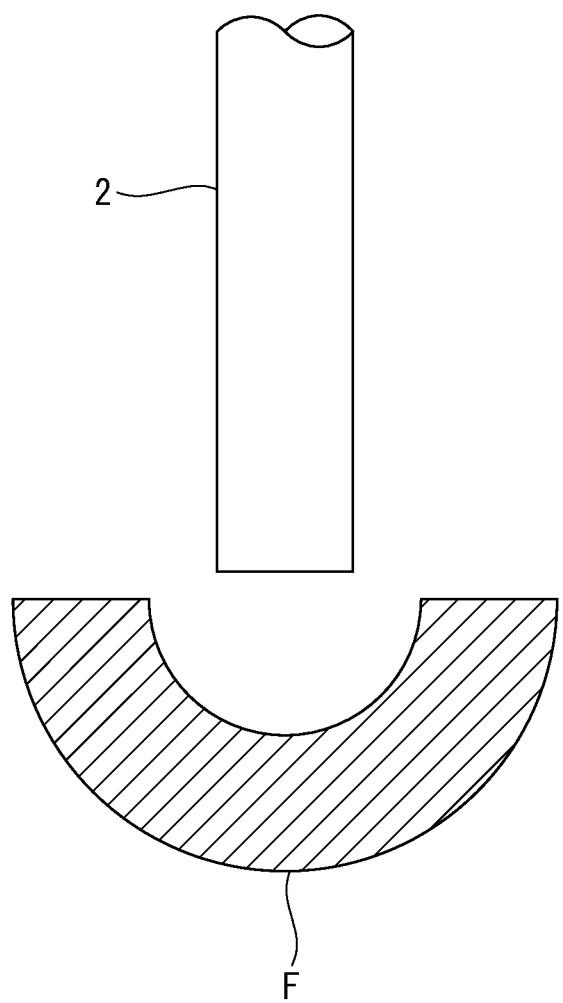
FIG. 13 is a diagram showing one example of a phantom used in an image processing method and an endoscope observation method that are performed with the image processing device in FIG. 1.

In addition, as shown in FIG. 13, the surface irradiated with light emitted from the endoscope 2 should preferably have a shape similar to the shape of biological tissue serving as an observation subject. By doing so, color transformation can be performed in the same manner as for actual biological tissue by taking into account the influence of scattering in the interior of the tissue.

Figure 14:
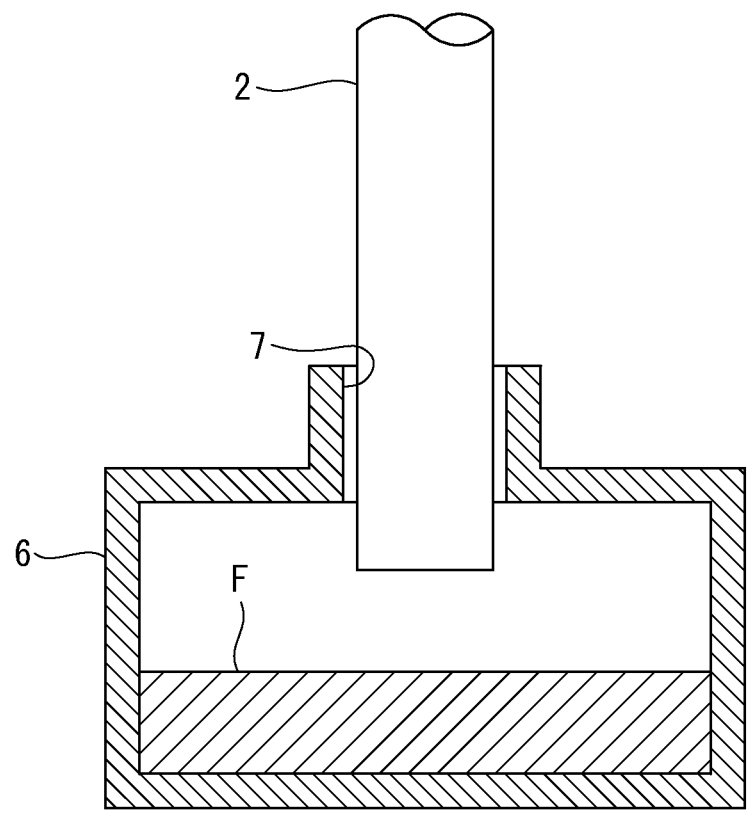
FIG. 14 is a diagram showing another example of a phantom used in an image processing method and an endoscope observation method that are performed with the image processing device in FIG. 1.

In addition, as shown in FIG. 14, the phantom F may be accommodated in a container 6 that blocks ambient light, and the container 6 may include an opening 7 through which the endoscope 2 can be inserted into the container 6. By doing so, color transformation can be performed while realizing an environment mimicking an actual environment in the living body shielded from ambient light.

Figure 15:
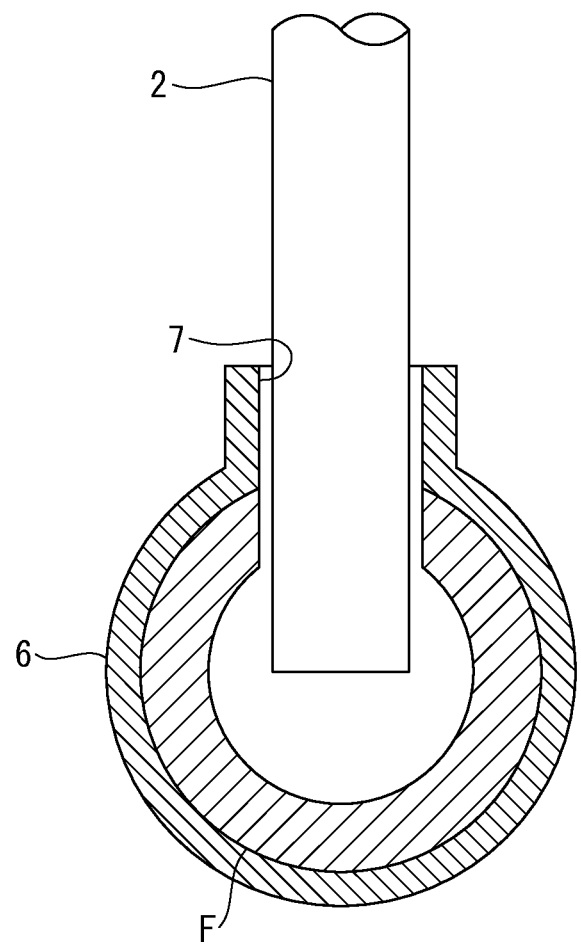
FIG. 15 is a diagram showing another example of a phantom used in an image processing method and an endoscope observation method that are performed with the image processing device in FIG. 1.

Furthermore, as shown in FIG. 15, the phantom F disposed in the container 6 that blocks ambient light may have a shape similar to the shape of biological tissue serving as an observation subject. As seen typically with a spherical shape, such as the shape of the bladder, or a cylindrical shape, such as the shape of the digestive tract, an actual organ has a stereoscopic inner shape. Therefore, a phantom F formed of a material that is uniform over the entire shape similar to the shape of biological tissue may be provided. By doing so, color transformation can be performed by taking into account hue variations depending on the distance and the angle between the endoscope 2 and the phantom F during actual observation.

As a result, the above-described embodiment leads to the following aspects.

One aspect of the present invention is directed to an image processing device including: a parameter calculation unit that calculates, on a basis of a reference image acquired by capturing an image of a reference subject including optical characteristics of an imaging living body, a parameter for transforming, into an achromatic color through congruence transformation in a color space, a color corresponding to a target region included in the reference image defined in the color space; and a transformation unit that performs, in the color space on a basis of the parameter calculated by the parameter calculation unit, the congruence transformation of the colors of a color image acquired by capturing an image of the living body, the color image being constituted by luminance information of at least two wavelength bands having different center wavelengths.

According to this aspect, the parameter calculation unit calculates, on the basis of a reference image acquired by capturing an image of a reference subject including optical characteristics of a living body, a parameter for transforming, into an achromatic color through congruence transformation in a color space, a color of a target region in the reference image defined in the color space. Also, the parameter calculated by the parameter calculation unit is used in the transformation unit, which transforms the colors of the color image acquired by capturing an image of the living body. Here, an achromatic color is white, black, and a color obtained by mixing white and black, i.e., a color containing gray with various color densities.

By setting a target region included in the living body, a parameter for transforming a color of the set target region into an achromatic color through congruence transformation in the color space is calculated, and the color of a site other than the set target region is shifted to a different color on the basis of the calculated parameter. By doing so, the difference between the set target region and the site other than the set target region can be made more noticeable as the difference between an achromatic color and a chromatic color. Furthermore, because the distance in the color space between the set target region and the site other than the set target region is not changed, it is possible to prevent an extreme color difference between the set target region and the site other than the set target region. In short, when a physician diagnoses a boundary between a target region and a non-target region, it is possible to assist the physician by facilitating visual recognition of subtle changes in the hue of the living body while maintaining stability in the accuracy of the physician's diagnosis.

In the above-described aspect, the transformation unit may perform, on the colors of the color image, at least one transformation of translation movement and rotational movement in the color space.

This configuration allows the target region to be transformed into an achromatic color, either by translation movement or by rotational movement of the color image, without changing the distance in the color space between the set target region and the site other than the set target region, thereby facilitating visual recognition of changes in a subtle hue of the living body.

In the above-described aspect, the reference subject may be a phantom mimicking the optical characteristics of the living body.

With this configuration, it is possible to easily determine a target region in the reference image acquired by capturing an image of a reference subject composed of a phantom mimicking optical characteristics of the living body and quickly obtain the parameter used in the transformation unit.

With this configuration, even when the image-capturing unit for capturing images is replaced with another, it is possible to stably calculate the parameter used in the transformation unit. In addition, temporal changes in the characteristics of the living body can also be grasped with high accuracy by calculating a transformation parameter by using a phantom with stable characteristics. This makes it easier for a physician to determine disease conditions and do post-therapy follow-up.

Because the parameter for a component constituting the phantom corresponds to optical characteristics of the phantom, a component of the living body can be simulatively estimated from an image generated on the basis of a parameter that is obtained by using this phantom and that is used in the transformation unit. This can assist the physician in diagnosis by analogically inferring a change in the pathological structure of the living body.

In the above-described aspect, the target region may be a normal site included in the living body.

With this configuration, the physician can quickly obtain the parameter used in the transformation unit merely by specifying a normal site as a target region in the reference image.

In the above-described aspect, the reference subject may be the imaging living body, and the reference image may be an image including a normal site of the living body.

In the above-described aspect, the target region may be a region of a normal mucosa, the region having a relatively smaller number of blood vessels.

In the above-described aspect, the target region may be a blood vessel site.

In the above-described aspect, the target region may be a normal mucosa around abnormal tissue.

In the above-described aspect, the target region may be a fat site.

Another aspect of the present invention is directed to an image processing device including: a processor, wherein the processor calculates, on a basis of a reference image acquired by capturing an image of a reference subject including optical characteristics of an imaging living body, a parameter for transforming, into an achromatic color through congruence transformation in a color space, a color corresponding to a target region included in the reference image defined in the color space and performs, in the color space on a basis of the calculated parameter, the congruence transformation of the colors of a color image acquired by capturing an image of the living body, the color image being constituted by luminance information of at least two wavelength bands having different center wavelengths.

Another aspect of the present invention is directed to an image processing method including: calculating, on a basis of a reference image acquired by capturing an image of a reference subject including optical characteristics of an imaging living body, a parameter for transforming, into an achromatic color through congruence transformation in a color space, a color corresponding to a target region included in the reference image defined in the color space; and performing, in the color space on a basis of the parameter obtained by calculation, the congruence transformation of all colors of a color image acquired by capturing an image of the living body, the color image being constituted by luminance information of at least two wavelength bands having different center wavelengths.

Another aspect of the present invention is directed to an endoscope system including: an image-capturing unit that acquires the color image by capturing an image of the living body; and one of the above-described image processing devices, wherein the parameter calculation unit calculates the parameter on a basis of the reference image acquired by capturing an image of the reference subject by means of the image-capturing unit, and the transformation unit transforms the colors of the color image acquired by the image-capturing unit.

The above-described aspect may include a phantom mimicking the optical characteristics of the living body, wherein the reference subject may be the phantom.

Another aspect of the present invention is directed to an endoscope observation method including: acquiring a reference image by capturing, by means of an endoscope, an image of a reference subject including optical characteristics of a living body; calculating, on a basis of the acquired reference image, a parameter for transforming, into an achromatic color through congruence transformation in a color space, a color of a target region included in the reference image defined in the color space; acquiring a color image constituted by luminance information of at least two wavelength bands having different center wavelengths by capturing an image of the living body by means of the endoscope; performing the congruence transformation of all colors of the acquired color image in the color space on a basis of the parameter acquired by calculation; and displaying an image that has been subjected to the congruence transformation.

In the above-described aspect, the reference subject may be a phantom mimicking the optical characteristics of the living body.

In the above-described aspect, the phantom may have a shape mimicking a shape of the living body.

In the above-described aspect, the phantom may be disposed in a container that blocks ambient light, and the container may have an opening through which the endoscope can be inserted into the container.

The present invention provides an advantage in that it is possible to facilitate visual recognition of subtle changes in the hue of a living body while maintaining stability in the accuracy of a physician's diagnosis.

REFERENCE SIGNS LIST

1 Endoscope system
2 Endoscope (image-capturing unit)
3 Image processing device
6 Container
7 Opening
31 Control unit (processor)
32 Parameter calculation unit (processor)
34 Image transformation unit (transformation unit, processor)
35 Image generation unit (processor)
C Color image
F Phantom (reference subject)
R3 Third region (target region)

The invention claimed is:
1. An image processing device comprising:
one or more processors comprising hardware, the one or more processors being configured to:
calculate, on a basis of a reference image acquired by capturing an image of a reference subject which has an optical characteristic that is equivalent to at least a part of a living body, image transformation parameters through congruence transformation that transforms a coordinate corresponding to a color of target region included in the reference image defined in a color space into a coordinate corresponding to an achromatic color in the color space; and perform, in the color space on a basis of the calculated image transformation parameters, the congruence transformation of colors of a color image acquired by capturing an image of the living body, the color image being constituted by at least two monochromatic image corresponding to different illumination having different center wavelengths.

2. The image processing device according to claim 1, wherein the congruence transformation performs, on the colors of the color image, at least one transformation of translation movement and rotational movement in the color space.

3. The image processing device according to claim 1, wherein the reference subject is a phantom mimicking the optical characteristics of the living body.

4. The image processing device according to claim 1, wherein the target region is a site included in the living body clinically diagnosed as normal.

5. The image processing device according to claim 1, wherein the reference subject is the living body, and
the reference image is an image including a site of the living body clinically diagnosed as normal.

6. The image processing device according to claim 1, wherein the target region is a region of a normal mucosa, the region having a relatively smaller number of blood vessels.

7. The image processing device according to claim 1, wherein the target region is a blood vessel site.

8. The image processing device according to claim 1, wherein the target region is a normal mucosa around abnormal tissue.

9. The image processing device according to claim 1, wherein the target region is a fatty tissue site.

10. An endoscope system comprising:
the image processing device according to claim 1,
an endoscope that acquires the color image by capturing the image of the living body; and
wherein the calculating of the image transformation parameters calculates the image transformation parameters on a basis of the reference image acquired by capturing the image of the reference subject by the endoscope, and
the performing of the congruence transformation transforms the colors of the color image acquired by the endoscope.

11. The endoscope system according to claim 10, comprising:
a phantom mimicking the optical characteristic of the living body,
wherein the reference subject is the phantom.

12. An image processing method comprising:
calculating, on a basis of a reference image acquired by capturing an image of a reference subject which has an optical characteristic that is equivalent to at least a part of a living body, image transformation parameters through congruence transformation that transforms a coordinate corresponding to a color of target region included in the reference image defined in a color space into a coordinate corresponding to an achromatic color in the color space; and performing, in the color space on a basis of the image transformation parameters obtained by calculation, the congruence transformation of colors of a color image acquired by capturing an image of the living body, the color image being constituted by at least two monochromatic image corresponding to different illumination having different center wavelengths.

13. An endoscope observation method comprising:
acquiring a reference image by capturing, by an endoscope, an image of a reference subject which has an optical characteristic that is equivalent to at least a part of a living body;
calculating, on a basis of the acquired reference image, image transformation parameters through congruence transformation that transforms a coordinate corresponding to a color of a target region included in the reference image defined in a color space into a coordinate corresponding to an achromatic color in the color space;
acquiring a color image constituted by at least two monochromatic image corresponding to different illumination having different center wavelengths by capturing an image of the living body by the endoscope;
performing the congruence transformation of all colors of the acquired color image in the color space on a basis of the image transformation parameters acquired by calculation; and
displaying an image that has been subjected to the congruence transformation.

14. The endoscope observation method according to claim 13, wherein the reference subject is a phantom mimicking the optical characteristic of the living body.

15. The endoscope observation method according to claim 14, wherein the phantom has a shape mimicking a shape of the living body.

16. The endoscope observation method according to claim 14, wherein the phantom is disposed in a container that blocks ambient light, and the container has an opening through which the endoscope can be inserted into the container.

* * * * *